United States Patent [19]

Villeneuve

[11] 4,322,382
[45] Mar. 30, 1982

[54] METALLURGICAL MOUNT PREPARATION METHOD

[76] Inventor: Norman R. Villeneuve, 84 Newgate Rd., East Granby, Conn. 06026

[21] Appl. No.: 162,386

[22] Filed: Jun. 23, 1980

[51] Int. Cl.³ .......................... B29C 6/02; B29C 1/04
[52] U.S. Cl. ...................................... 264/279; 249/78; 264/275; 264/279.1
[58] Field of Search .................. 249/78; 264/271, 275, 264/279, 331.12, 271.1, 279.1; 425/117

[56] References Cited

U.S. PATENT DOCUMENTS

| | | | |
|---|---|---|---|
| 2,776,596 | 1/1957 | Eigen | 264/279 |
| 3,185,432 | 5/1965 | Hager, Jr. | 249/78 |
| 3,234,595 | 2/1966 | Weichselbaum et al. | 425/117 |
| 3,268,466 | 8/1966 | Simm | 264/331.12 |
| 3,349,158 | 10/1967 | Maynard | 264/279 |
| 3,358,064 | 12/1967 | Belko, Jr. | 264/331.12 |
| 3,678,141 | 7/1972 | Metcalfe | 264/331.12 |
| 3,996,326 | 12/1976 | Schachet | 264/275 |
| 4,158,090 | 6/1979 | Sabourin et al. | 264/331.12 |

Primary Examiner—James B. Lowe
Attorney, Agent, or Firm—McCormick, Paulding & Huber

[57] ABSTRACT

A method for preparing solid metallurgical mounts uses a surface in heat exchange relationship with mounting molds placed thereon and with an initially liquid mounting agent contained in the molds. The surface is defined by a block of polytetrafluoroethylene exposed to a source of heat. As part of the molding operation, the surface is preheated and maintained at a substantially constant temperature throughout the operation. The molding operation includes mixing of a quantity of epoxy resin and a hardener, pouring the mixture into a mold or molds and curing the mixture at an elevated temperature in contact with the polytetrafluoroethylene surface.

6 Claims, 4 Drawing Figures

METALLURGICAL MOUNT PREPARATION METHOD

BACKGROUND OF THE INVENTION

This invention relates to a method for preparing metallurgical mounts, such as are used to hold metallurgical specimens while the specimens are being viewed under a microscope, and deals more particularly with such a method and apparatus utilizing a heat curing liquid mounting agent and an agent curing surface defined by a block of polytetrafluoroethylene which is heated throughout the agent pouring and curing steps.

The type of method with which this invention is concerned is one which may be used for preparing a metallurgical mount from a mixture of liquid resin and hardener poured into a mounting mold containing a specimen. At the beginning of the molding operation, an empty mounting mold, usually in the form of a ring having an inner diameter of one-half to two inches, is placed on a generally horizontal surface and a metallurgical specimen is placed on the surface within the mounting mold. Subsequently, a liquid mounting agent consisting of a resin and hardener is poured into the mold. The agent is then cured to a hardened state before being removed from the mold as an easy-to-manage mount. The hardened mount may then be ground, lapped, or otherwise treated to prepare a surface of the contained specimen for viewing under a microscope.

At the present time there are many different known ways of enbedding a metallurgical specimen in a surrounding body of solid material in order to make it more manageable, and a good number of these known procedures include the use of a hardenable, initially liquid, mounting agent which in some cases may be cured at room temperature and in other cases at an elevated temperature. Most of the known methods, however, have one or more disadvantages such as a long curing time, the release of odorous vapors during mixing and/or curing of the agent, the need for precise measurement of the agent components, the use of costly materials and the production of finished mounts having undesirable characteristics such as poor adhesion between the mounting agent and the specimen, lack of transparency in the mounting agent, and poor behavior of the mounting agent under grinding or lapping conditions.

It is a general object of the invention to provide an improved method which avoids the above-mentioned disadvantages and which can be used to produce superior metallurgical mounts at low cost.

SUMMARY OF THE INVENTION

This invention resides in a method for preparing metallurgical specimen mounts. The assosciated apparatus includes a generally horizontal support surface defined by a block of polytetrafluoroethylene on which open bottomed annular mounting molds are placed, and a heat source beneath and in heat transfer relationship with the block. The heat source includes regulating means for controlling the temperature of the support surface. A base surrounds the sides of the heat source and is insulated thermally and electrically from it.

The method of the invention includes the steps of preparation of metallurgical mounts utilizing apparatus. Open-bottomed mounting molds are placed on a block of polytetrafluoroethylene, a metallurgical specimen is placed within the mold and flush against the surface of polytetrafluoroethylene, the block is heated to a temperature above ambient, and an uncured mounting agent (preheated or not) is poured into the mold and allowed to cure while the block is maintained at the heated temperature.

DETAILED DESCRIPTION OF THE PREFERRED EMBODIMENTS

Figure 2:
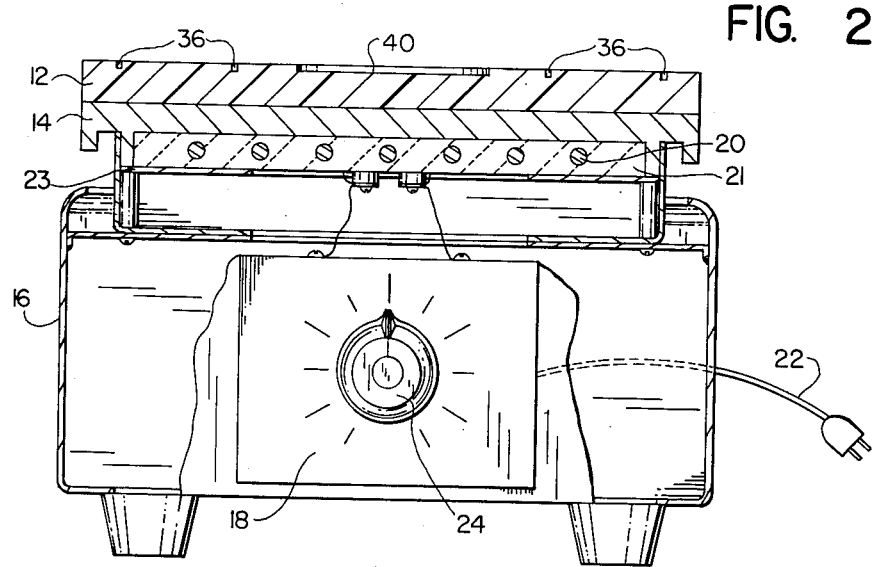
FIG. 2 is a view partly in vertical section and partly in elevation showing the unit of FIG. 1.
Figure 1:
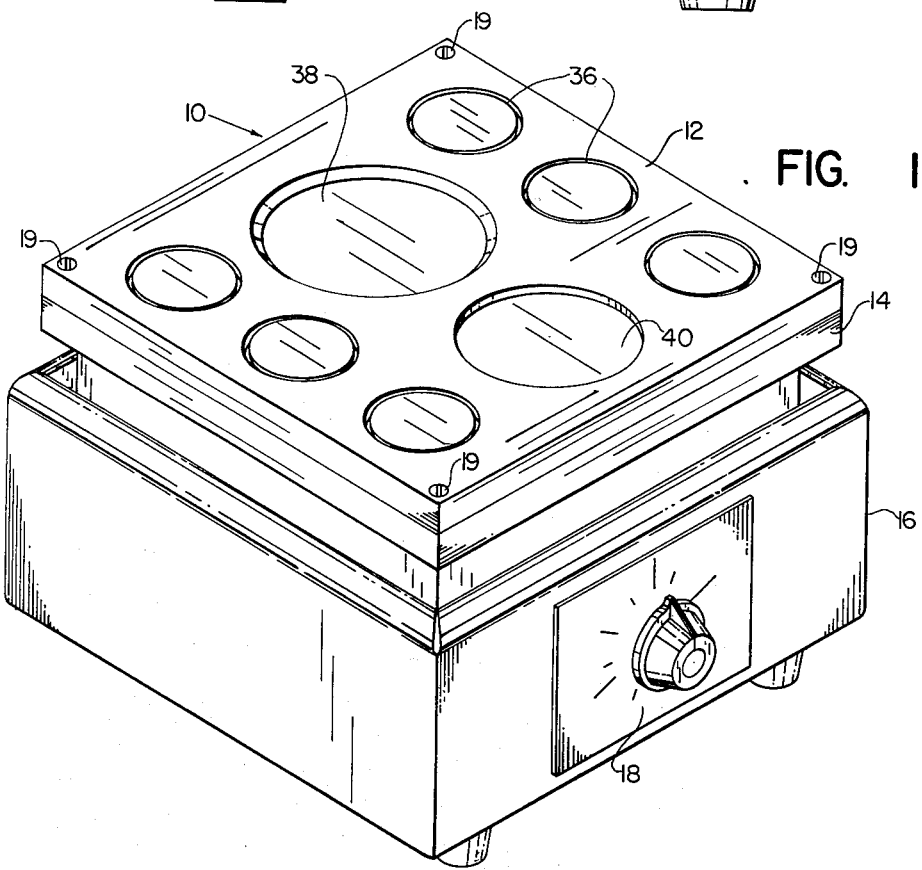
FIG. 1 is a perspective view of a metallurgical mount heating unit used in practicing the present invention.

FIG. 1 shows a unit 10 designed for practicing the present invention. This unit includes a block of polytetrafluoroethylene 12, a metallic plate 14, a base 16, and an electrical control 18. The block of polytetrafluoroethylene 12 is in the form of a rectangular flat plate, which is preferably at least one-quarter inch in thickness, and which is positioned horizontally to define a top surface on which metallurgical mounting molds may be placed. The block 12 is vertically supported by the plate 14 and is fastened to it by any suitable means such as the illustrated screws 19, 19. The metallic plate 14 is rectangular and has an upper face of generally the same size and shape as the lower surface of the block 12 so that the two are in good heat transfer relation with one another. In FIG. 2, the engagement of the block 12 with the supporting plate 14 is shown in a cross-sectional view. The supporting plate is preferably made of a metal, such as steel, which conducts heat easily.

Figure 3:
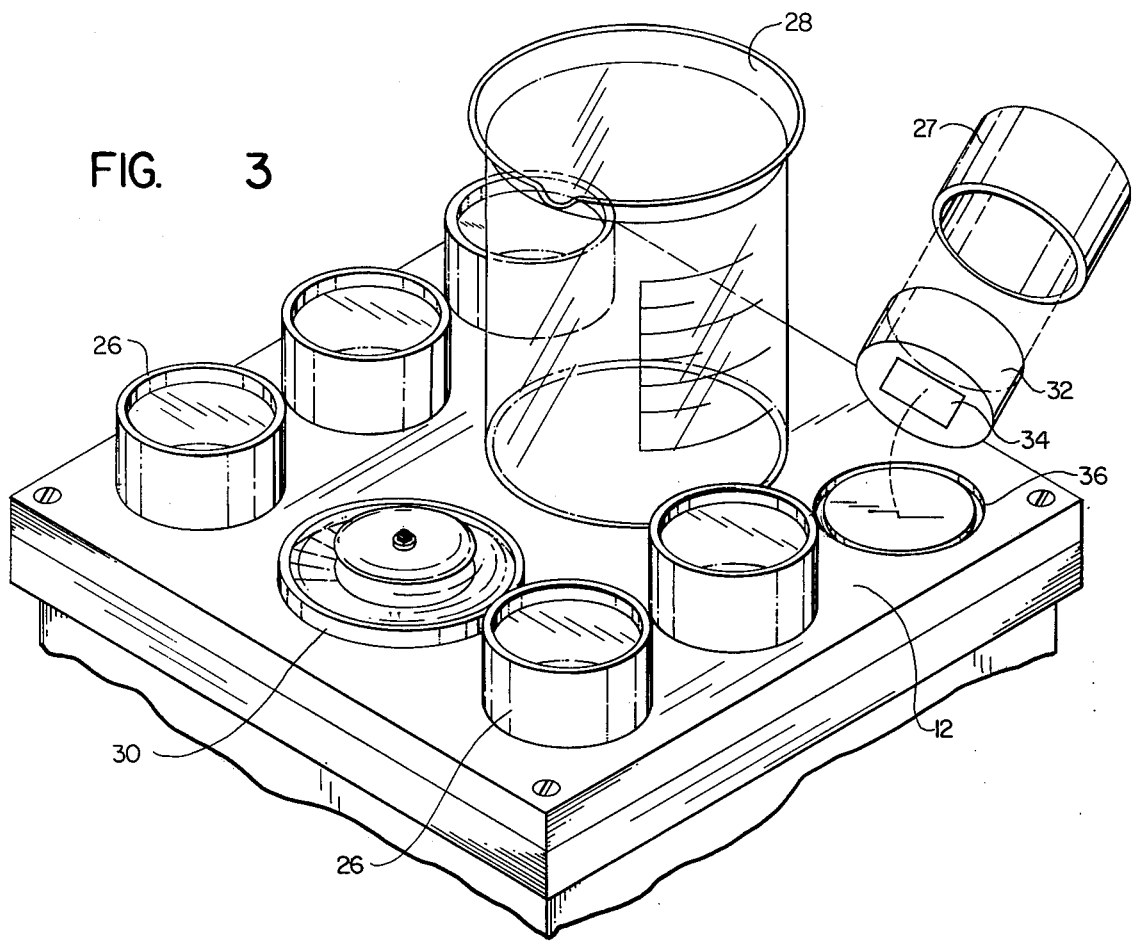
FIG. 3 is a fragmentary perspective view of the top of the unit of FIG. 1 and shows associated metallurgical mounting paraphernalia used in practicing the invention.

An elongated electric heating element 20, as shown in FIG. 2, is contained in a serpentine pattern within an asbestos plate 21 which is held against the lower surface of the metallic plate 14 by a frame 23. The element 20 is wired at each end to the electrical control 18 which has an input lead 22 for connection to an electrical supply outlet. In the illustrated case the electrical control 18 through an associated adjustment knob 24 controls the power supplied to the heating element 20 and thereby regulates the temperature of the polytetrafluoroethylene block 12. That is, after the knob 24 is set to one setting the block 12 will soon thereafter reach a stable temperature which will be generally maintained until the knob is readjusted to another position. However, if desired the control 18 may also include a thermostat associated with the block 12 for still more closely regulating its temperature. In FIG. 3 five mounting molds 26, 26 are shown containing mounting agent and undergoing the curing process. An identical mold 27 is shown elevated from the top surface of the block 12 and a finished product in the form of a mount 32 with an embedded specimen 34 is shown removed from the mold.

FIG. 3 shows a typical arrangement of mount molding paraphernalia placed upon the top surface of block 12. Included among this paraphernalia are molds 26, 26, a beaker 28, and a surface thermometer 30. The mounting molds 26, 26 are in the form of annular rings with open bottoms and tops which allow contact between the block 12 and the metallurgical specimen placed within each mold. With a specimen in place in a mold and the block 12 preheated to a temperature above ambient, preferably at least 100° F., a mounting agent consisting of a liquid resin, preferably an epoxy resin, and hardener is poured into that mold and allowed to cure while the preheated temperature of the block 12 is maintained. The surface thermometer 30 allows for the monitoring of the block temperature.

Preferably, and in accordance with one method of the invention, the liquid resin portion of the mounting agent is heated to the curing temperature, that is the temperature of the block 12, prior to its mixture with the hardener and to the pouring of the mixture into the mold. For most conveniently carrying out this heating step the liquid resin is placed in the beaker 28 and heated upon the surface of the block 12. Hardener is then added to all or some of this heated resin, preferably in a separate mixing container into which all or some of the resin from the beaker 28 is poured, and the two components are stirred thoroughly, after which the mixture is poured into the awaiting mold or molds.

Figure 4:
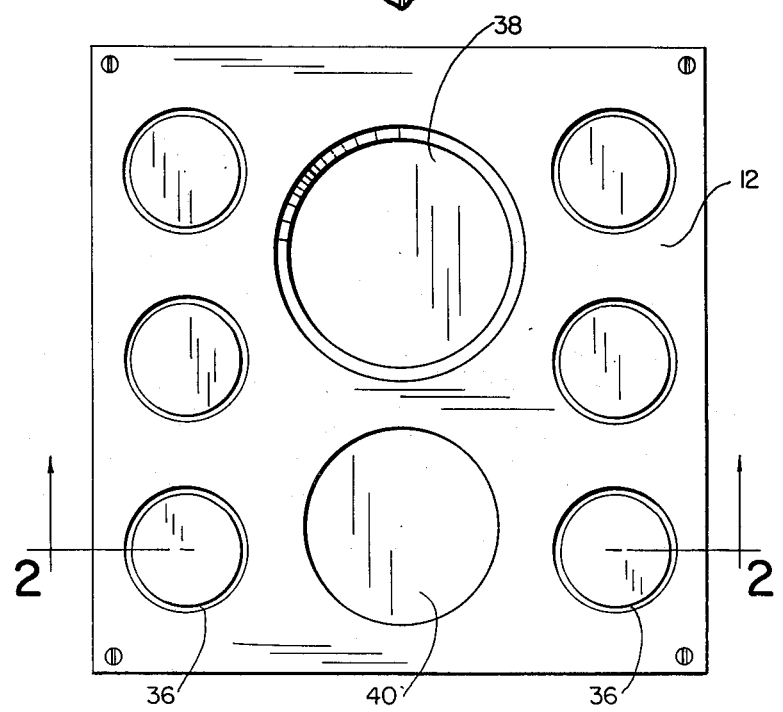
FIG. 4 is a plan view of the unit of FIG. 1.

Another feature of the invention is that the top surface of the block 12 contains shallow recesses for the molding paraphernalia, a typical arrangement of which is shown in FIGS. 1 and 4. For the beaker and thermometer these recesses are in the form of indented circular areas 38 and 40. For the molds 26, 26 the illustrated recesses are in the form of circular grooves 36, 36 which receive the lower ends of the associated molds with an easy sliding fit. Alternatively, however, the recesses for the molds may also be indented circular areas similar to those for the beaker and thermometer, but sized to fit the molds. As seen in the cross-sectional view of the block 12 in FIG. 2, the recesses are of relatively shallow depth.

I claim:

1. A method for preparing metallurgical mounts, said method comprising the steps of:
   providing a block of polytetrafluoroethylene defining a supporting surface on which mounting molds may be placed in a molding operation,
   placing on said supporting surface an open-bottomed mounting mold having a bottom area considerably smaller than the area of said supporting surface,
   heating said block of polytetrafluoroethylene to raise said supporting surface to an elevated temperature above ambient temperature,
   placing a metallurgical specimen on said supporting surface within said mounting mold,
   providing a mounting agent in the form of an uncured liquid mixture of resin and hardener,
   pouring said uncured mounting agent into said mounting mold so as to fill at least a portion of said mold and to surround at least a portion of said specimen while also contacting said supporting surface of said block of polytetrafluoroethylene through said open bottom of said mold, and
   heating said block of polytetrafluoroethylene to maintain substantially said elevated temperature of said supporting surface while said mounting agent is allowed to cure.

2. A method for preparing metallurgical mounts as described in claim 1 wherein:
   said elevated temperature above ambient temperature is at least 100° F.

3. A method for preparing metallurgical mounts as described in claim 1 wherein said resin is an epoxy resin.

4. A method for preparing metallurgical mounts as described in claim 1 or claim 3, wherein:
   said resin is heated to said elevated temperature prior to mixing with said hardener to form said mounting agent.

5. A method for preparing metallurgical mounts as described in claim 1 or claim 3, wherein:
   said resin is heated to said elevated temperature by placing it and an associated container for it on said supporting surface for some time prior to said pouring step, and by maintaining said elevated temperature of said supporting surface while said resin and its container are received thereon.

6. A method for preparing metallurgical mounts as described in claim 1 wherein:
   said block of polytetrafluoroethylene has a thickness of about one-quarter inch or more.

* * * * *